(12) United States Patent  (10) Patent No.: US 7,835,795 B2
Alexander et al.  (45) Date of Patent: Nov. 16, 2010

(54) LEAD RETENTION ASSEMBLY

(75) Inventors: James A. Alexander, Shorewood, MN (US); Shahn Sage, Andover, MN (US)

(73) Assignee: Medtronic, Inc., Minneapolis ( * ) Notice: Subject to any disclaimer, the term of this patent is extended or adjusted under 35 U.S.C. 154(b) by 715 days.

(21) Appl. No.: 11/737,498

(22) Filed: Apr. 19, 2007

(65) Prior Publication Data

US 2008/0262564 A1 Oct. 23, 2008

(51) Int. Cl.
*A61N 1/375* (2006.01)

(52) U.S. Cl. .......................................... 607/37; 439/817

(58) Field of Classification Search ................. 607/116, 607/37; 439/816, 817
See application file for complete search history.

(56) References Cited

U.S. PATENT DOCUMENTS

| | | | |
|---|---|---|---|
| 5,257,622 A | 11/1993 | Hooper | |
| 5,261,395 A | 11/1993 | Oleen | |
| 5,275,620 A | 1/1994 | Darby | |
| 5,957,968 A | 9/1999 | Belden | |
| 2006/0127158 A1 | 6/2006 | Olson | |
| 2006/0173520 A1 | 8/2006 | Olson | |

FOREIGN PATENT DOCUMENTS

EP 0356721 3/1990

OTHER PUBLICATIONS

PCT Search Report dated Jul. 15, 2008.

*Primary Examiner*—Carl H Layno
*Assistant Examiner*—Jeremiah T Kimball
(74) *Attorney, Agent, or Firm*—Campbell, Nelson, Whipps, LLC

(57) ABSTRACT

A lead retention assembly includes first, second and third retention members. The first retention member defines a first opening configured to receive a lead body. The second retention member is longitudinally spaced apart from the first retention member and defines a second opening configured to receive the lead body. The first and second retention members are substantially aligned along a first axis. The third retention member defines a third opening configured to receive the lead body. The third retention member is disposed between the first and second retention members and is biased in a position such that the third opening is substantially centered on a second axis. Upon application of a compressive force, the third retention member is moveable to a position such that the first, second, and third openings are substantially aligned along a common axis, allowing the lead body to be inserted within the first, second and third openings.

12 Claims, 7 Drawing Sheets

LEAD RETENTION ASSEMBLY

FIELD

This application relates to medical devices, more particularly implantable leads and retention assemblies for coupling leads to lead extensions or electrical signal generators.

BACKGROUND

Implantable electrical signal generators, such as pacemakers, defibrillators, neurostimulators, and the like, have been used to treat a variety of diseases. Such devices generate electrical signals that are transferred to a patient's tissue through electrodes disposed on a distal end portion of a lead. The proximal end portion of the lead typically contains a number of connector rings corresponding to the number of electrodes. Conductors run within and along the lead body and electrically couple the connectors to the electrodes. The proximal end portion of the lead is inserted into connector of a signal generator such that electrical contact is made between discrete contacts in the connector portion and the connector rings of the lead. Alternatively, the lead is inserted into connector region of a lead extension. Like the connector portion of a signal generator, the lead extension connector region is configured such that electrical contact is made between discrete contacts in the connector region and the connector rings of the lead. The proximal portion of the lead extension contains electrical connections that are electrically coupled to the contacts in the connector region and serve to electrically couple electrodes of a lead to the signal generator when the lead is connected to the lead extension and the extension is inserted into the connector of the signal generator.

Regardless of whether the lead is inserted into an extension or an electrical signal generator, the lead is secured in place with a set screw to prevent the lead from being unintentionally pulled out of the signal generator or lead extension. A torque wrench is typically employed to ensure proper tightening of the set screw. Use of a torque wrench to tighten a set screw of a device implanted in a patient can be awkward. If the set screw, whether used with the connector portion of an electrical signal generator or lead extension, serves to electrically couple the signal generator or extension to the lead, a polymeric boot is sutured on either end of the connector region to prevent stimulation of the tissue in proximity to the set screw.

BRIEF SUMMARY

Lead retention assemblies that may be used to secure leads without the use of a torque wrench are described herein. A compressive force is applied to the connector assembly to allow the lead to be inserted into the connector assembly. Upon release of the compressive force, the connector assembly engages and retains the lead.

In various embodiments, a lead retention assembly having first, second and third retention members is described. The first retention member defines a first opening configured to receive a lead body. The second retention member is longitudinally spaced apart from the first retention member and defines a second opening configured to receive the lead body. The first and second retention members are substantially aligned along a first axis. The third retention member defines a third opening configured to receive the lead body. The third retention is disposed between the first and second retention members and is biased in a position such that the third opening is substantially centered on a second axis. Upon application of a compressive force, the third retention member is moveable to a position such that the first, second, and third openings are substantially aligned along a common axis, allowing the lead body to be inserted within the first, second and third openings. Devices, such as implantable signal generators, lead extensions or other adaptors having the lead retention assembly are also described.

In various embodiments, a system including a lead and an implantable medical device having a connector for receiving and operbaly coupling the lead is described. The lead has a lead body, a proximal end portion, and a distal end portion. The proximal end portion has a recipient feature. The connector of the implantable medical device includes first, second and third retention members. The first retention member defines a first opening configured to receive the lead body. The second retention member is longitudinally spaced apart from the first retention member and defines a second opening configured to receive the lead body. The first and second openings are substantially aligned along a first axis. The third retention member defines a third opening configured to receive the lead body and is disposed between the first and second retention members. The third retention member is biased in a position such that the third opening is substantially centered on a second axis. One or more of the first, second or third retention members includes a protruding element extending into a portion of the first, second or third opening. Upon application of a compressive force, the third retention member is moveable to a position such that the first, second and third openings are substantially aligned along a common axis, allowing the lead body to be inserted within the first, second and third openings. Upon relaxing the compressive force, the protruding element is received by the recipient feature of the lead, longitudinally securing the lead relative to the implantable medical device.

By providing a lead retention assembly that (i) allows a lead to be inserted upon application of a compressive force and (ii) engages and retains the lead upon release of the compressive force, surgical steps during implantation of an electrical signal generator system may be reduced. For example, steps of tightening a small set screw with a torque wrench and electrically isolating the set screw by suturing a boot may be eliminated. These and other advantages will be readily understood from the following detailed descriptions when read in conjunction with the accompanying drawings.

Figure 1:
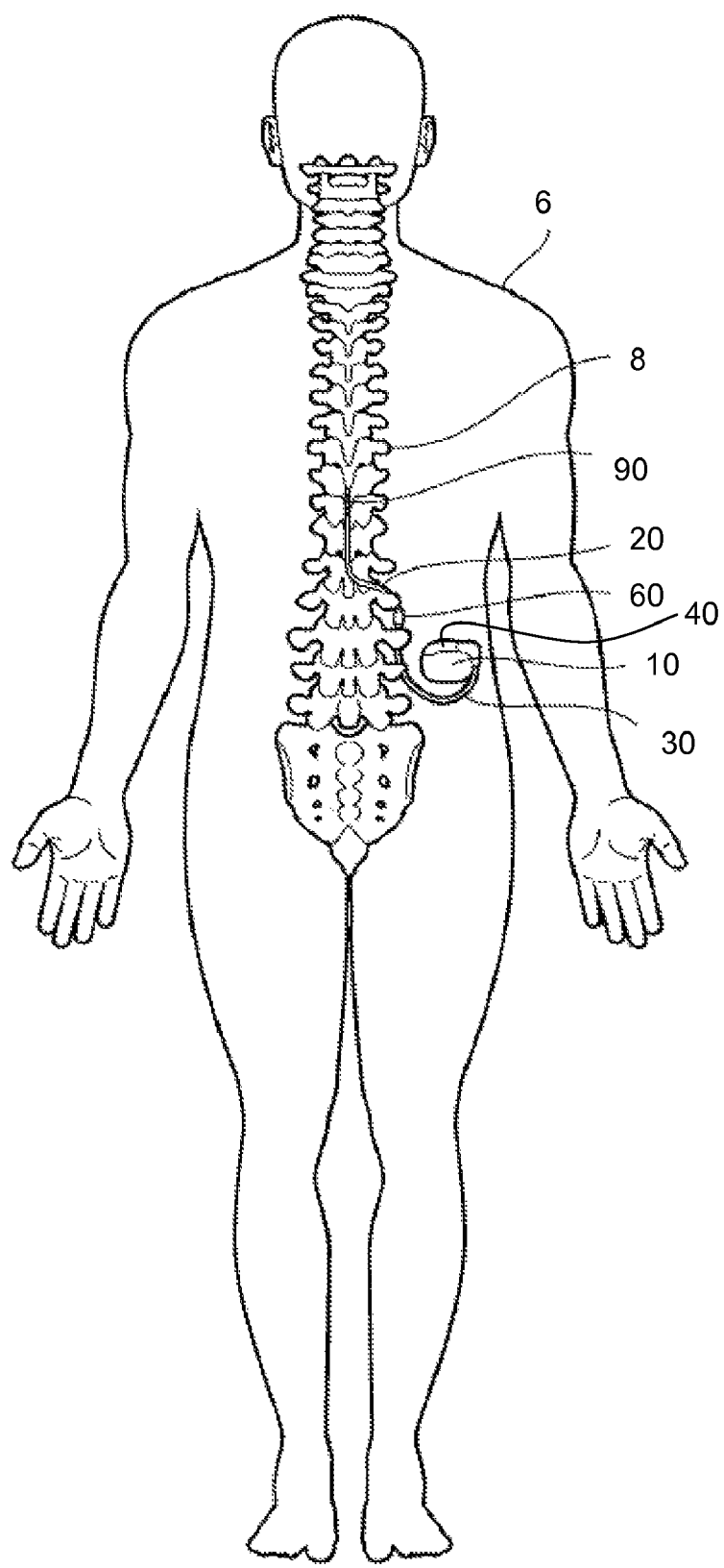
FIG. 1 is a diagrammatic representation of an environment of a representative spinal cord stimulation (SCS) system implanted in a patient.

The drawings are not necessarily to scale. Like numbers used in the figures refer to like components, steps and the like. However, it will be understood that the use of a number to refer to a component in a given figure is not intended to limit the component in another figure labeled with the same number.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope of spirit of the present invention. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "proximal" and "distal" refer to position relative to an implantable electrical signal generator. For example, a proximal portion of a lead is a portion nearer a signal generator, and a distal portion is a portion further from the signal generator.

As used herein, "substantially align", as it refers to retention members along an axis, means that the retention members are positioned such that a portion of a lead may be inserted in openings formed by the substantially aligned retention members. When not substantially aligned, the lead is prevented from being inserted in openings.

As used herein, "active electrical device" means a device having a power source and electronics operably coupled to the power source, where the electronics are capable of generating or receiving an electrical signal.

The present disclosure relates to implantable medical devices, such as implantable electrical signal generators and lead extensions that are used to secure and electrically couple leads so that electrical stimulation signals may be reliably applied to a patient tissue via electrodes of the lead. More particularly, the disclosure relates to lead retention assemblies that may be used to secure leads relative to signal generators, lead extensions or adaptors. The retention assemblies form a part of, or are connected to, the signal generators, lead extensions or other adaptors. A compressive force is applied to the assemblies to allow the lead to be inserted into the assembly. Upon release of the compressive force, the lead is retained by the retention assembly and thus relative to the signal generator, lead extension or adaptor.

Referring to FIG. 1, a spinal cord stimulation (SCS) system, is shown implanted in a patient 6. For SCS, an implantable electrical signal generator 10 is typically placed in the abdominal region of patient 6 and lead 20 is placed at a desired location along spinal cord 8. A lead extension 30 operably couples signal generator 10 to lead 20. Connector block 40 of signal generator 10 electrically couples and secures lead extension 30. Connector region 60 of lead extension 30 electrically couples and secures lead 20. Signal generator 10 contains a power source and electronics for sending electrical signals to the spinal cord 8 via electrodes 90 of lead 20 to provide a desired therapeutic or diagnostic effect. Such a system, or any system including an active electrical device 10 as described herein, may also include a programmer (not shown), such as a physician programmer or a patient programmer capable of wireless communicating with signal generator 10.

It will be appreciated that systems other than SCS systems employing active electrical devices and therapeutic uses thereof are contemplated. For example, active electrical device 10 may be any electrical signal generator or receiver useful for delivering therapy to a patient or for patient diagnostics. By way of example, active electrical device 10 may be a monitoring device; hearing implant; a cochlear implant; a sensing device; a signal generator such as a cardiac pacemaker or defibrillator, a neurostimulator (such as a spinal cord stimulator, a brain or deep brain stimulator, a peripheral nerve stimulator, a vagal nerve stimulator, an occipital nerve stimulator, a subcutaneous stimulator, etc.), a gastric stimulator; or the like.

Figure 2:
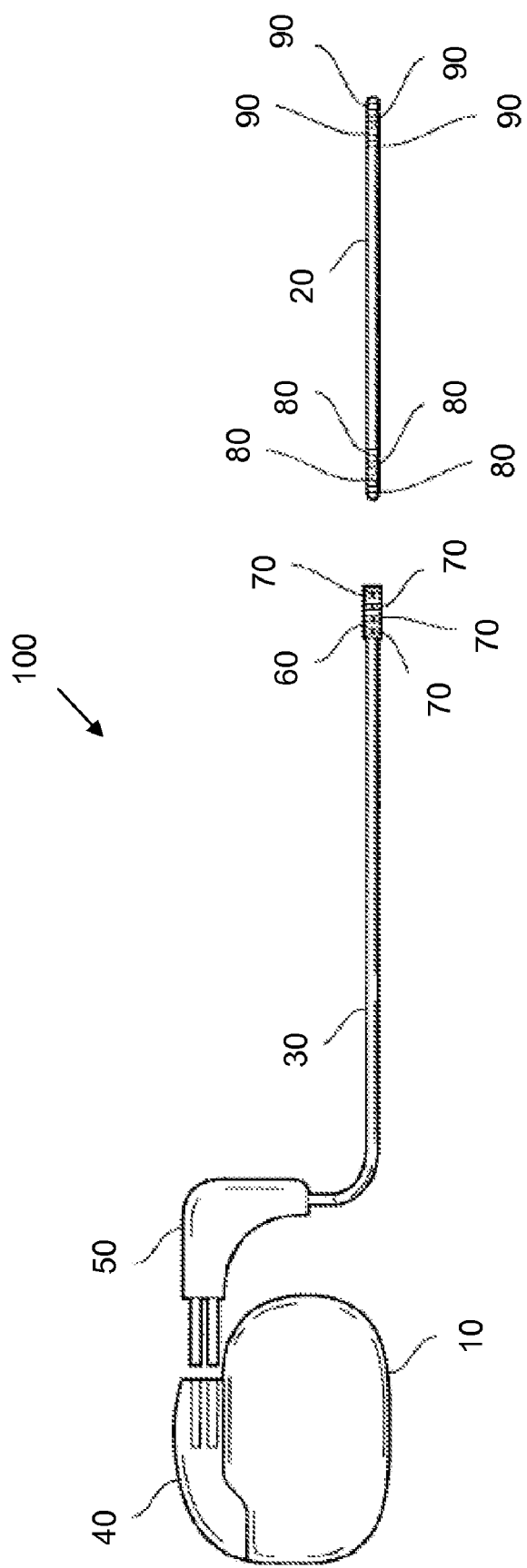
FIG. 2 a diagrammatic representation of an exploded view of a representative implantable electrical signal therapy system.

Referring to FIG. 2, an exploded view of a representative implantable active electrical system 100 is shown. In the system shown in FIG. 2, implantable active electrical device 10 comprises a connector block 40 configured to receive proximal end portion 50 of extension 30. The distal end portion of extension 30 comprises a connector region 60 configured to receive proximal end of lead 20. Connector region 60 comprises internal electrical contacts 70 configured to electrically couple extension 30 to lead 20 via electrical contacts 80 disposed on the proximal end portion of lead 20. Electrodes 90 are disposed on distal end portion of lead 20 and are electrically coupled to electrical contacts 80, typically through conductors (not shown). Lead 20 may include any number of electrodes 90, e.g. one, two, three, four, five, six, seven, eight, sixteen, thirty-two, or sixty-four. Typically, each electrode 90 is electrically coupled to a discrete electrical contact 80.

While not show in FIG. 1 or 2, it will be understood that lead 20 may be coupled to active electrical device 10 without lead extension 30 or other adaptor. It will be further understood that more than one lead 20 may be operably coupled to one active electrical device 10 or one extension 30 or that more than one extension 30 may be operably coupled to one active electrical device 10.

Figure 3:
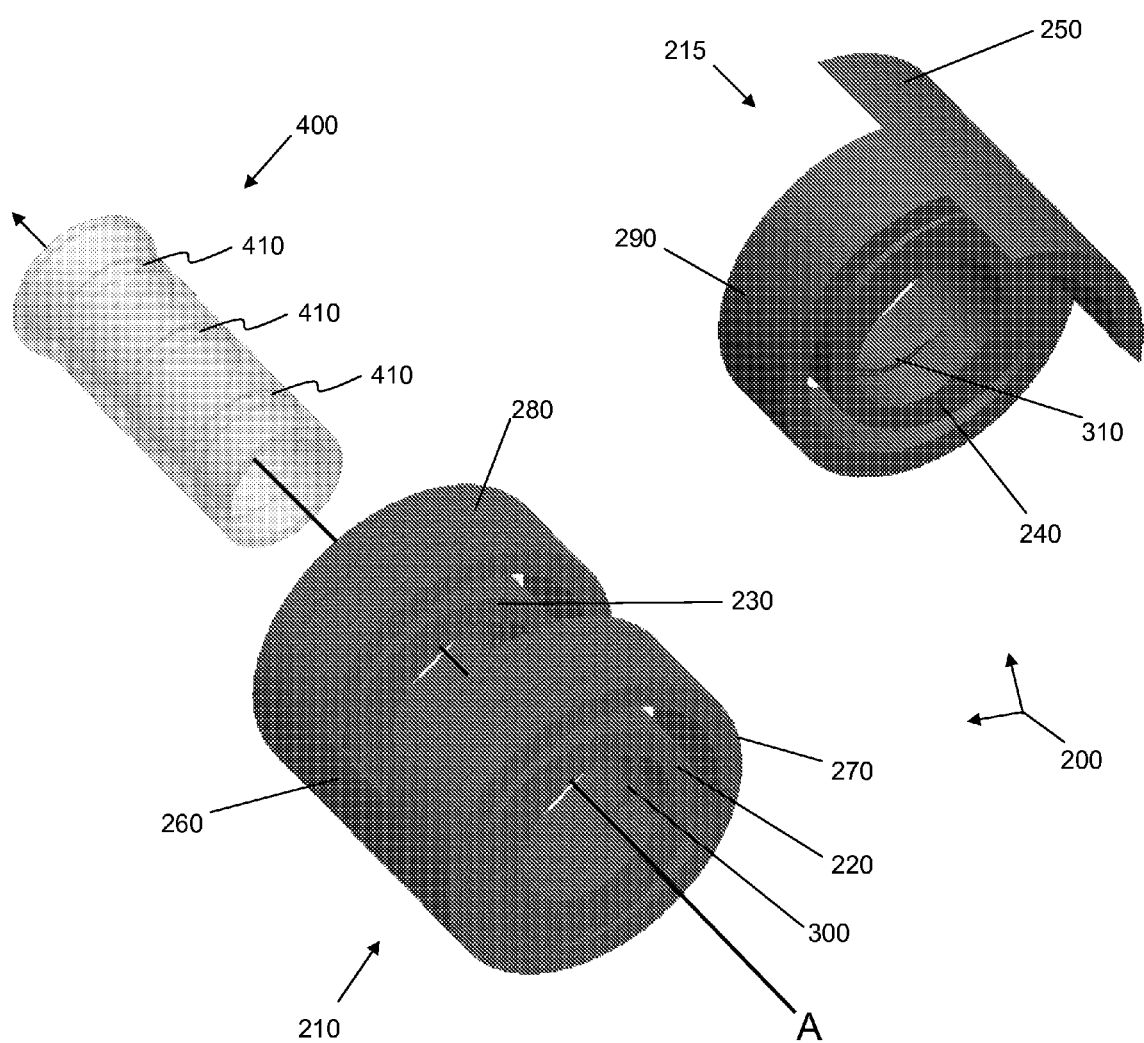
FIG. 3 is a diagrammatic representation of an exploded view of a representative lead retention assembly.

Referring to FIG. 3, a diagrammatic representation of an exploded view of a representative lead retention assembly 200 is shown. Lead retention assembly 200 includes first 220, second 230, and third 240 retention members. First retention member 220 defines a first opening configured to receive a lead body. Second retention member 230 is longitudinally spaced apart from first retention member 220 and defines a second opening configured to receive the lead body. Alignment element 260 aligns first 220 and second 230 retention members such that the first and second openings are substantially aligned along a first axis (e.g., as shown by the line A in FIG. 3). Third retention member 240 defines a third opening configured to receive the lead body and is longitudinally disposed between first 220 and second 230 retention members in use.

Figure 4A:
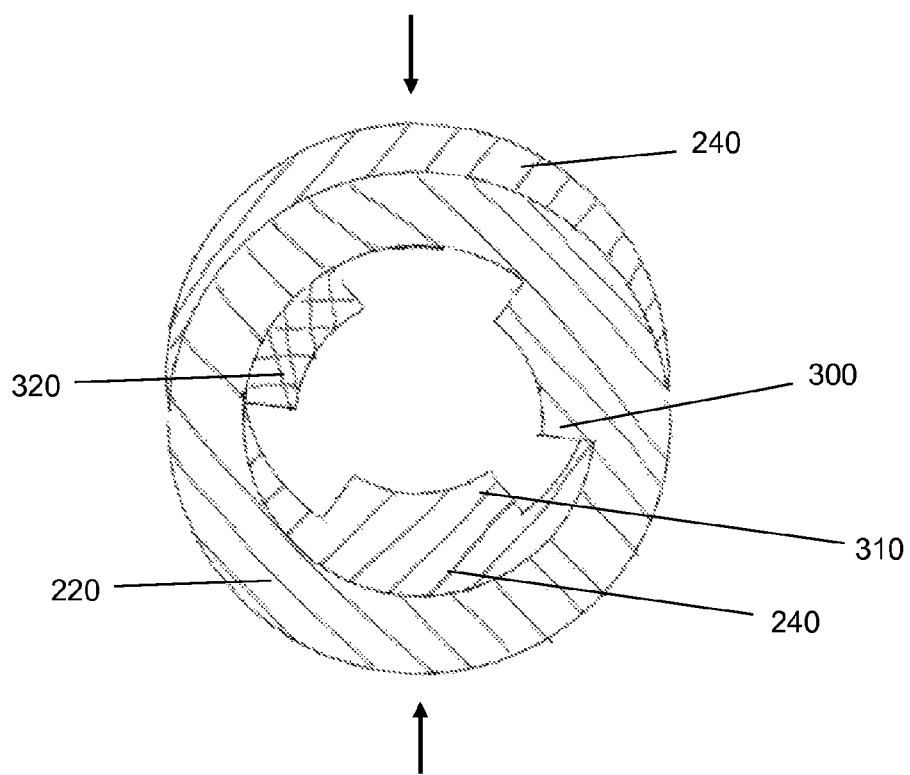
FIGS. 4A-B are diagrammatic representations of isolated head-on views of retention members of a representative lead assembly in an uncompressed (4A) and compressed (4B) state.
Figure 4B:
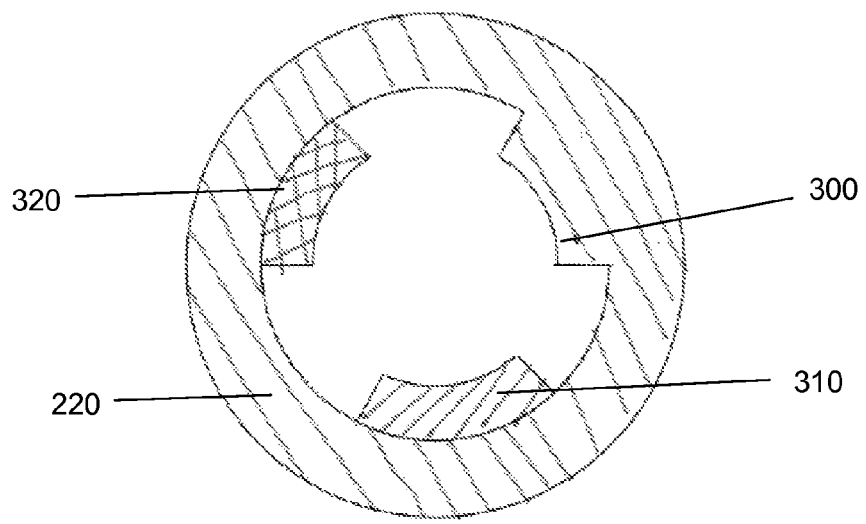

Referring to FIGS. 4A-B, head-on views (e.g., along the axis shown by line A in FIG. 3) of retention members 220, 230, 240 of representative lead assembly in an uncompressed (4A) and a compressed (4B) state are shown. As shown in FIG. 4, in use, third retention member 240 is biased (in its relaxed state 4A) in a position such that the third opening is substantially centered on a second axis, different from the first axis on which the first and second openings of first 220 and second 230 members are aligned. Upon application of a compressive force (e.g., in the direction shown by the arrows in FIG. 4A), third retention member 240 is moveable to a position such that the first, second and third openings are aligned along a common axis (see FIG. 4B), allowing the lead body to be inserted within the first, second and third openings. Upon release of the compressive force, third retention member 240 returns or is biased towards the uncompressed configuration (FIG. 4A) to secure lead body within retention assembly 200.

Third retention member 240 may be biased in the position such that the third opening is substantially centered on a second axis (other than the first axis on which the first and second openings are substantially aligned) by any suitable biasing element. For example, and referring to FIG. 3, a deformable third outer member 290 may be disposed about and operably coupled to third retention member 240. In the embodiment depicted in FIG. 3, third deformable outer member 290 is attached to or formed with third retention member 240 along a surface in contact with or formed by an extension element 250. Extension element 250 may be pressed such that third outer member 290 (i) contacts alignment member 260 between first 220 and second 230 retention members and (ii) deforms to allow the openings of the first 220, second 230, and third 240 retention members to substantially align along a common axis, allowing a portion of lead to be inserted into the first, second and third openings. Lead retention assembly 200 may further include deformable first 270 or second 280 outer members disposed about and operably coupled to first 220 or second 230 retention members, respectively. In use, extension element 250 as depicted in FIG. 3 engages a portion of first 270 and second 280 deformable outer member such that compressive force applied to extension element 250 relative to first 270 and second 280 outer deformable members causes first 270 or second 280 outer members to deform, allowing alignment of the openings defined by first 220, second 230, and third 240 retention members. First 270, second 280, and third 290 deformable outer members may act cooperatively to bias third retention member 240 such that its opening is substantially centered on the second axis. Alternative configurations for biasing third retention member 240 such that its opening is substantially centered on the second axis are described in more detail with regard to FIG. 8.

In the embodiment shown in FIG. 3, lead retention assembly 200 contains two parts, a first part 210 and a second part 215. First 210 or second 215 parts may contain a plurality of pieces or may be formed of a single piece. First part 210 includes first 220 and second 230 retention members and alignment member 260. First part 210 may also include first 280 or second 290 outer deformable members. Second part 215 includes third retention member 240 and extension element 250 and may also include third outer deformable member 290. Retention members and deformable outer members may be molded or extruded together from the same or different material, may be welded, adhered, bonded or otherwise connected. In various embodiments, one or more retention members are formed from conductive material. Any suitable conductive material may be used to form retention members. For example, the retention member may be formed from a nickel-cobalt base alloy, such as MP35N. Of course, the components of first part 210 or second part 215 may be formed of conductive material, non-conductive material, or a composite of materials. In an embodiment, the entire retention assembly 200 is formed from a conductive metal alloy. One of skill in the art will readily understand which materials may be selected to form retention assembly 200 or components thereof based on the functions performed by the various components. For example, outer members 270, 280, 290 should be made of material capable of deforming sufficiently to allow openings of first 220, second 230, and third 240 retention members to substantially align along a common axis.

Figure 5:
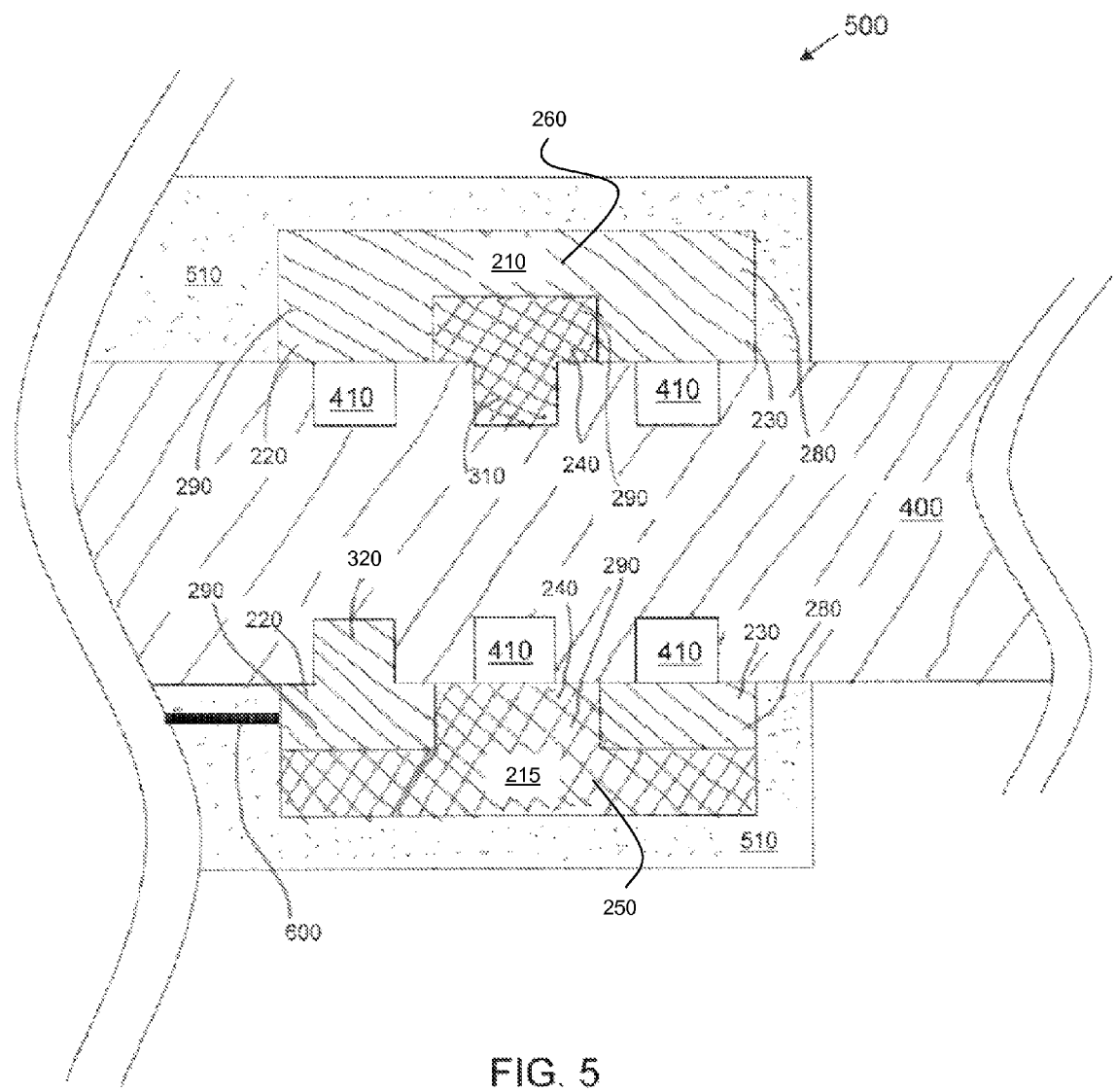
FIG. 5 is a diagrammatic representation of a longitudinal section of some components of a representative lead assembly with a secured lead.

Referring now to FIGS. 3-5, one or more retention members 220, 230, 240 may contain one or more protruding elements that extend into the openings defined by the retention members. For example, first retention member 220 may contain a first protruding element 300, second retention element 230 may contain a second protruding element 320, and third retention member 240 may contain a third protruding element 310. Protruding elements 310, 320, 330 are configured to be received by recipient features 410, such as a groove, of a portion 400 of lead 20. While protruding elements 300, 310, 330 shown in FIG. 4 are roughly equally radially spaced, it will be understood that nearly any radial spacing of protruding elements 300, 310, 330 will serve to secure lead 20 relative to retention assembly 200. However, in embodiments employing more than one protruding element 300, 310, 330, it may be desirable for at least two of the protruding elements 300, 310, 330 to be at least somewhat radially spaced apart to more securely retain the lead.

FIG. 5 is a diagrammatic representation of a longitudinal section of some components of a representative lead retention assembly 200 with a portion 400 of lead 20 secured. Lead retention assembly 200 is shown in the embodiment depicted in FIG. 5 as being located in a connector 500 of an implantable device. Connector 500 may be, for example, connector block 40 of active electrical device 10 or connector region 60 of lead extension 30 as depicted in FIG. 1 or FIG. 2. Lead retention assembly 200 is shown in FIG. 5 in a compressed state, with protruding elements 310, 320 being received by recipient features 410 (groves) of portion 400 of lead 20. Body material 510 of connector 500 serves to keep the first part 210 and second part 215 of retention assembly 200 from separating. Of course, it will be understood that a polymeric sleeve or the like may also serve such a purpose. In various embodiments (not shown), retention assembly 200 is not entirely covered by body material 510 or sleeve of connector 500 but is bonded, adhered, fastened, molded into or otherwise affixed to body material 510 of connector 500 of device, which once lead 20 is captured in retention assembly 200 serves to secure the lead relative to the device. Regardless, the portion of connector 500 in the region of retention assembly 200 is compressibly deformable. While lead retention assembly 200 will serve to secure lead 200 without protruding elements 300, 310, 320 (and corresponding recipient features 410 on lead), the ability to longitudinally retain lead 20 by assembly 200 is greatly enhanced by the presence of protruding elements 300, 310, 320 (and corresponding recipient features 410 on lead).

In various embodiments, lead retention assembly 200 or portion thereof is electrically coupled to a device of which it forms a part. For example, and as shown in FIG. 5, a conductor 600 within connector 500 of the device may be electrically coupled to a retention member (shown as connected to first retention member 220). In such embodiments, the retention member is made of a conductive material. If connector 500 is a part of an implantable active electrical device 10, a conductor 600 may be fed through a feedthrough (not shown) to electrically couple assembly 200 to electronics of the device 10. If connector is part of a lead extension 30, connector may be an internal contact 70 of extension 30.

While not shown, it will be understood that if the portion 400 of the lead shown in FIG. 5 is distal to an electrical contact 80 (see, e.g., FIG. 2), a conductor will be run through lead body along the portion 400 shown to electrically connect the contact 80 with an electrode 90. Of course, retention assembly 200 may engage lead 20 at nearly any location relative to contacts 80. For example, retention assembly may be proximal to, intermediate of or distal to contacts of lead (or serve as proximal, distal or intermediate contact). If portion 400 of lead shown in FIG. 5 includes a contact 80 (e.g., disposed about at least a portion of surface in contact with a conductive retention member or conductive protruding element), a conductor (not shown) will run along the lead body and connect contact 80 (not shown in FIG. 5) to an electrode 90 (See, e.g., FIG. 2). In various embodiments where portion 400 of lead 20 includes a contact 80, the contact 80 is formed into lead body material or bonded, secured, fastened, adhered or otherwise connected to lead body material. The contact 80 may include one or more recipient features 410 configured to receive one or more protruding element 300, 310, 330.

FIG. 5 depicts retention members 220, 230, 240 and protruding elements 310, 320 as being in contact with portion 400 of lead, which may be desirable for configurations where retention assembly 200 retains lead 20 by compressive biasing force (e.g., in embodiments lacking protruding elements 300, 310, 330) or where electrical contact between a conductive retention member 220, 230, 240 or protruding element 300, 310, 330 and at least a portion 400 of lead is desired (e.g., in embodiments where portion 40 of lead includes a contact 80). However, it will be understood that when one or more retention members 220, 230, 240 include one or more protruding elements 300, 310, 330, retention assembly 200 may secure lead 20 via recipient features 410 without pressing against lead.

Figure 6:
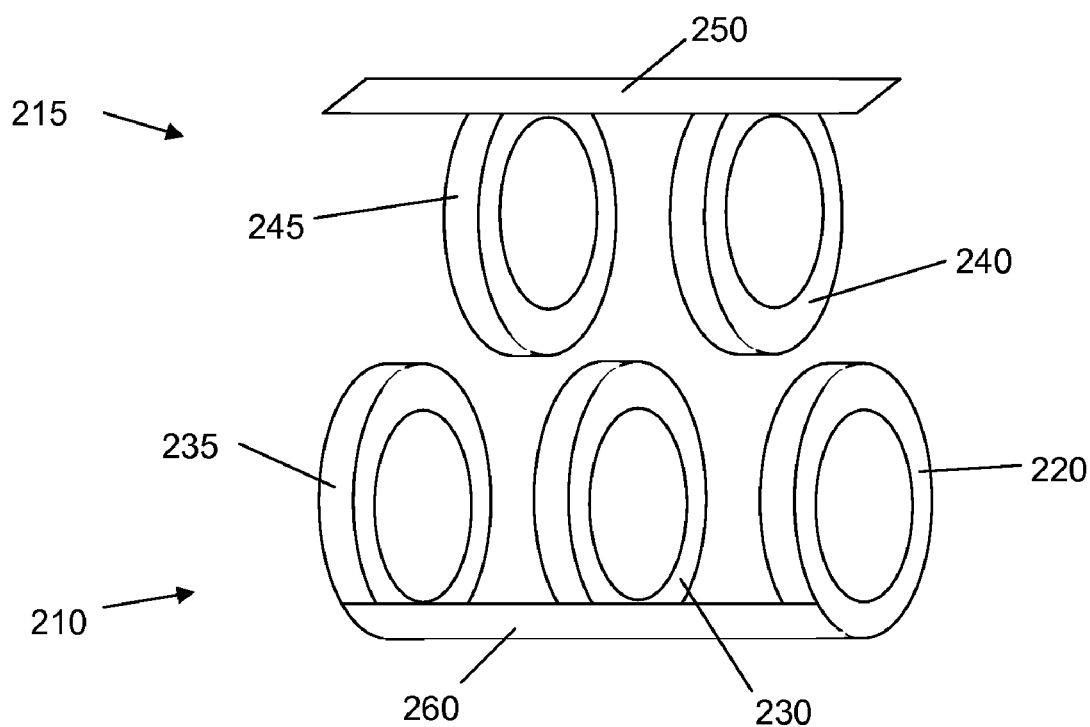
FIGS. 6-8 are line drawings of exploded views of representative lead retention assemblies or components thereof.
Figure 7:
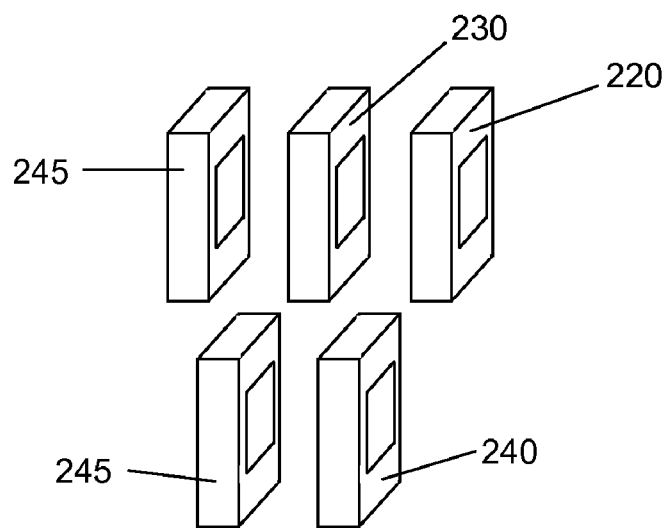

Referring to FIGS. 6-8, alternative embodiments of lead retention assemblies or components thereof are shown. A lead assembly as described herein may include any number of retention elements. For example, the embodiment depicted in FIG. 6 includes a total of five retention elements 220, 230, 235, 240, 245. The first part 210 includes three retention elements 220, 230, 235, and the second part 215 contains two retention elements 240, 245. While not shown, the first 210 or second part 215 may include one or more biasing element, such as an outer deformable member as shown in FIG. 3 or a biasing element as shown in FIG. 8.

Retention elements may be in any suitable shape for retaining a lead, depending on the shape of the lead. For example, in the embodiment depicted in FIG. 7 (only retention elements shown), the openings of retention elements 220, 230, 235, 240, 245 are generally cube-shaped.

Figure 8A:
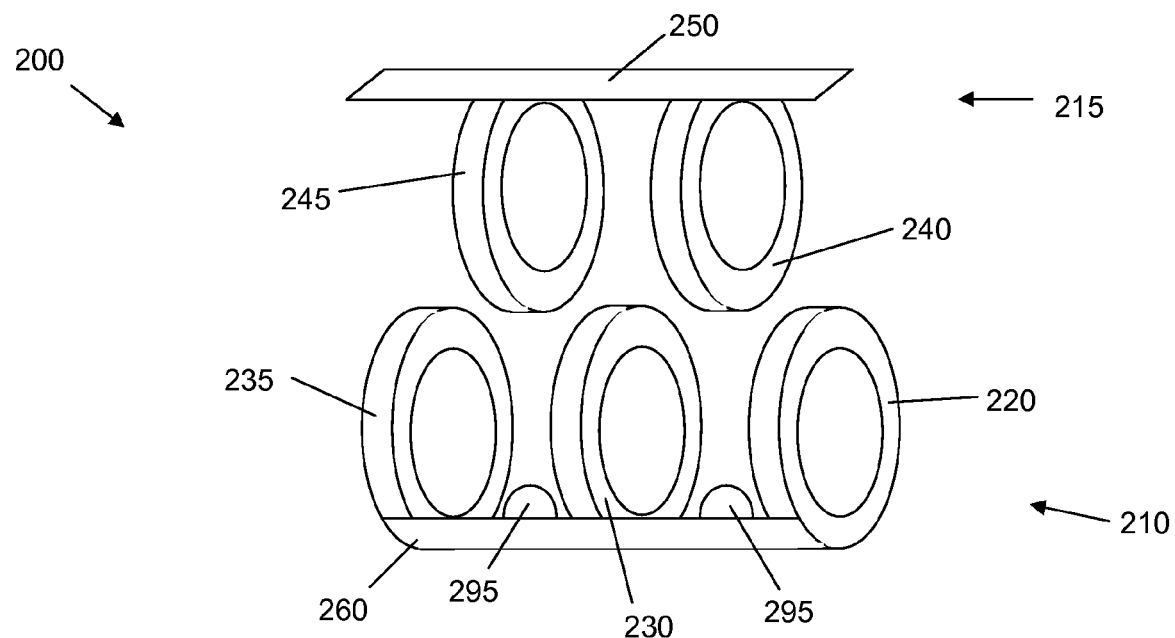

Referring to FIG. 8A, an embodiment of a retention assembly 200 is shown. First part 210 includes an alignment element 260 that substantially aligns openings of first 220, second 230, and fourth 235 retention members along a first axis. Second part 215 includes an extension element 250 that aligns openings of third 240 and fifth 245 retention members along a second axis (different from first axis). In use, the third retention member 240 is disposed between the first 220 and third 230 retention members and the fifth retention member 245 is disposed between the third 230 and fourth 235 retention members. The first part 210 also includes biasing elements 295 disposed on alignment element 260 between the first 220 and third 230 retention members and the third 230 and fourth 235 retention members. The biasing elements 295 are located such that, in use, they engage a portion of the third 240 and fifth 245 retention members. The biasing elements 295 bias the third 240 and fifth 245 retention members to a position such that openings formed by the third 240 and fifth 245 retention members are aligned along an axis different from the axis along which the first 220, second 230, and fourth 235 retention members are aligned. Application of a compressive force caused biasing members 295 to deform allowing the openings of the first 220, second 230, third 240, fourth 235, and fifth 245 retention members to be aligned along a common axis, allowing a lead to be inserted in the openings. Biasing elements 95 may be made of any deformable material and take any suitable form. For example, biasing elements 295 may be in the form of springs or the like.

Figure 8B:
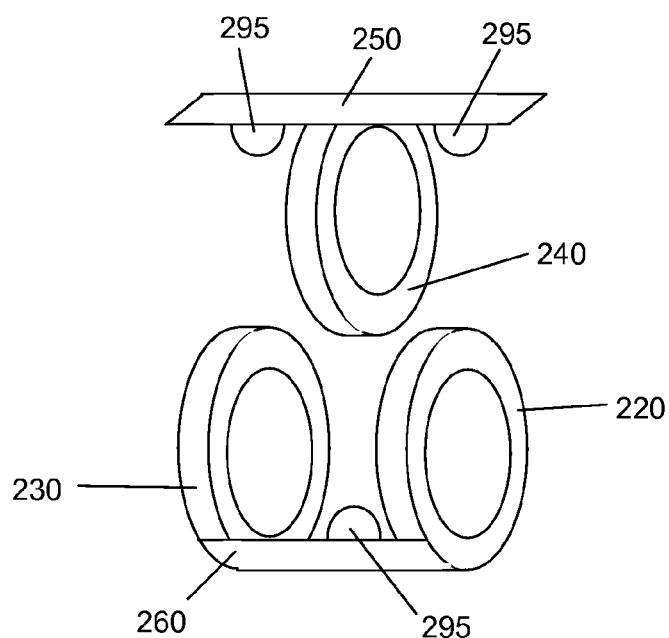

As shown in FIG. 8B, biasing elements 295 may be disposed on first part 210 and second part 215. Alternatively, biasing element 295 may be on either one of the first part 210 or second part 295.

While not shown in FIGS. 6-8, it will be understood that one or more retention elements 220, 230, 235, 240, 245 may include one or more protrusion elements.

Thus, embodiments of LEAD RETENTION ASSEMBLY are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A lead retention assembly comprising:
   a first part including
   (i) a first retention member defining a first opening configured to receive a lead body,
   (ii) a second retention member longitudinally spaced apart from the first retention member, the second retention member defining a second opening configured to receive the lead body,
   (iii) a deformable first outer member substantially concentric with the first retention member,
   (iv) a deformable second outer member substantially concentric with the second retention member, and
   (v) an alignment element operably coupled to the first and second outer members, wherein the alignment element is configured to maintain axial alignment of the first and second openings alone a first axis,
   wherein the first part is formed of conductive material and is configured to be electrically coupled to a conductor of a device of which the assembly forms a part; and
   a second part including
   (i) a third retention member defining a third opening configured to receive the lead body, the third retention member being disposed between the first and second retention members
   (ii) member substantially concentric with the third retention member, and
   (iii) an extension element operably coupled to the third outer member and configured to engage at least a portion of the first and second outer members in use,
   wherein the first, second and third outer members bias the third retention member such that the third opening is centered on a second axis
   wherein application of a compressive force to the assembly causes the first, second and third outer members to deform, allowing the third retention member to move to a position such that the first, second and third openings are aligned along a common axis, allowing the lead body to be inserted within the first, second and third openings.

2. The assembly of claim 1, wherein the first, second or third retention member comprises a protruding element extending into a portion of the first, second or third opening.

3. The assembly of claim 1, wherein the first retention member comprises a first protruding element extending into a portion of the first opening, wherein the second retention member comprises a second protruding element extending into a portion of the second opening, and wherein the third retention member comprises a third protruding element extending into a portion of the third opening.

4. An implantable medical device comprising:
a connector configured to receive and operably couple a lead to the device, the connector including a lead retention assembly according to claim 1,
wherein the connector is compressibly deformable to allow the third retention member to move to the position such that the first, second and third openings are substantially aligned along the common axis, allowing the lead body to be inserted within the first, second and third openings.

5. The device of claim 4, wherein the device is a lead extension.

6. The device of claim 4, wherein the device is an implantable electrical signal generator.

7. The implantable medical device of claim 4, further comprising a protruding element extending into a portion of the first, second, or third opening.

8. A system comprising:
a lead having a lead body, a proximal end portion, and a distal end portion, the proximal end portion comprising a recipient feature; and
an implantable medical device according to claim 7,
wherein, upon application of a compressive force, the third retention member is moveable to a position such that the first, second and third openings are substantially aligned along a common axis, allowing the lead body to be inserted within the first, second and third openings, and
wherein upon relaxing the compressive force, the protruding element is received by the recipient feature of the lead, longitudinally securing the lead relative to the implantable medical device.

9. The system of claim 8, wherein the implantable medical device is a lead extension.

10. The system of claim 8, wherein the implantable medical device is an electrical signal generator.

11. The system of claim 8, wherein the lead further comprises an electrical contact and the recipient feature is formed in the electrical contact.

12. The system of claim 8, wherein the recipient feature comprises a groove.

* * * * *

UNITED STATES PATENT AND TRADEMARK OFFICE
CERTIFICATE OF CORRECTION

| | | |
|---|---|---|
| PATENT NO. | : 7,835,795 B2 | Page 1 of 1 |
| APPLICATION NO. | : 11/737498 | |
| DATED | : November 16, 2010 | |
| INVENTOR(S) | : James A. Alexander | |

It is certified that error appears in the above-identified patent and that said Letters Patent is hereby corrected as shown below:

Column 8, Line 35
"openings alone a" should read -- openings along a --.

Column 8, Line 46
"(ii) member substantially" should read -- (ii) a deformable third outer member substantially --.

Signed and Sealed this
Twelfth Day of April, 2011

David J. Kappos
*Director of the United States Patent and Trademark Office*